United States Patent [19]

Luengo

[11] Patent Number: 5,362,735
[45] Date of Patent: Nov. 8, 1994

[54] RAPAMYCIN DERIVATIVES

[75] Inventor: Juan I. Luengo, Audubon, Pa.

[73] Assignee: SmithKline Beecham Corporation, Philadelphia, Pa.

[21] Appl. No.: 200,265

[22] Filed: Feb. 23, 1994

[51] Int. Cl.$^5$ .................. A61K 31/33; A61K 31/445; C07D 498/16
[52] U.S. Cl. ..................................... 514/291; 540/456
[58] Field of Search ......................... 540/546; 514/291

[56] References Cited

U.S. PATENT DOCUMENTS 5,102,876  4/1992  Caufield ............................. 514/183

Primary Examiner—Robert T. Bond
Attorney, Agent, or Firm—Yuriy P. Stercho; Stuart R. Suter; Edward T. Lentz

[57] ABSTRACT

Rapamycin derivatives; pharmaceutical compositions comprising such rapamycin derivatives and pharmaceutically acceptable carriers or excipients; and methods of using such derivatives to inhibit pathogenic fungi growth inhibition, inhibit immunosuppression or treat carcinogenic tumors are disclosed.

18 Claims, No Drawings

RAPAMYCIN DERIVATIVES

BACKGROUND OF THE INVENTION

This invention relates to rapamycin derivatives, pharmaceutical compositions comprising such derivatives, methods of treatment of disease states caused by pathogenic fungi, and methods of inducing desirable immunosuppression utilizing such rapamycin derivatives.

Rapamycin is a naturally occurring macrocyclic triene antibiotic which can be produced by culture techniques. Its structure may be illustrated as follows:

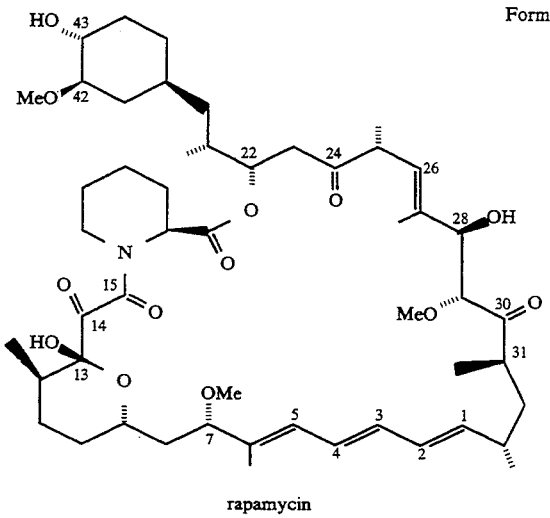

rapamycin

At least one rapamycin-producing strain of *Streptomyces hygroscopius* has been deposited with the Northern Utilization and Research Division, Agricultural Research Service, U.S. Department of Agriculture, Peoria, Ill., U.S.A. under accession number NRRL 5491. Rapamycin, and methods for its preparation by culturing NRRL 5491 are disclosed in U.S. Pat. No. 3,929,992, issued Dec. 30, 1975, the entire disclosure of which is hereby incorporated by reference.

There exist a variety of disease states in humans and other animals the treatment or prevention of which is benefitted by a therapeutic induction of immunosuppression. Such disease states include a whole host of inflammatory and autoimmune diseases and also include resistance to or rejection of transplanted organs.

Cyclosporine is widely used therapeutically when immunosuppression is desired, especially for the prevention of rejection of transplanted organs. However, cyclosporine is known to be nephrotoxic. Similarly, corticosteroids have long been used for immunosuppression, especially in the treatment of disease state caused by inflammation. However, corticosteroids are generally considered to exhibit a high systemic toxicity.

Amphotericins are used for the treatment of fungal infections. However, these compounds are nephrotoxic and lack a desirably broad spectrum of antifungal activity.

Thus, it may be appreciated that immunosuppressants and antifungal compounds having a more attenuated toxicity profile than the presently known therapeutic compounds are desirable.

SUMMARY OF THE INVENTION

I have recently discovered that novel rapamycin derivatives of the formula:

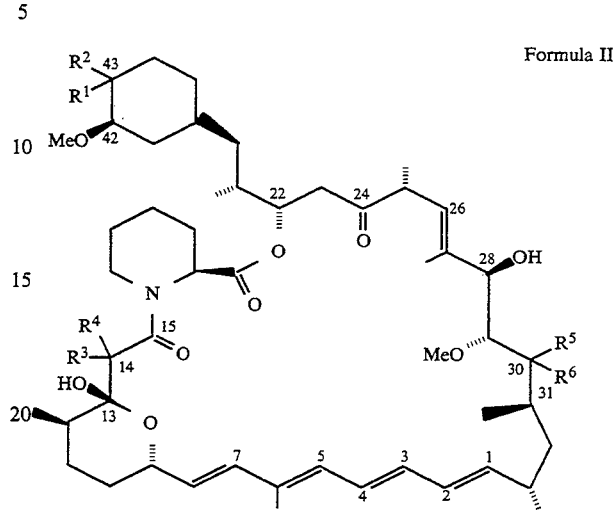

Formula II wherein:

$R^1$ and $R^2$ are selected from the group consisting of =O, (—OH,H) and (H,H);

$R^3$ and $R^4$ are selected from the group consisting of =O, (H,H) and (H,OH); and $R^5$ and $R^6$ are selected from the group consisting of =O and (H,OH); and all pharmaceutically acceptable salts, hydrates or solvates thereof.

This invention also relates to a pharmaceutical composition comprising an effective amount of one or more compounds of Formula II and a pharmaceutically acceptable carrier or excipient.

This invention also relates to a method of treatment of disease states caused by the growth of pathogenic fungi in a human or other animal; which method comprises administering an effective, non-toxic amount of one or more compounds of Formula II to a human or other animal in need thereof.

This invention also relates to a method of treatment for inducing therapeutically desirable immunosuppression in a human or other animal; which method comprises administering an effective, non-toxic amount of one or more compounds of Formula II to a human or other animal in need thereof.

DETAILED DESCRIPTION OF THE INVENTION

When any substituent (e.g., aryl, alkoxyl, $R^1$, $R^2$, $R^3$, $R^5$, or $R^6$) occurs more than one time in the formula for any of the compounds of Formula II, the definition of such substituent for a given occurrence is independent of its definition at every other occurrence, unless otherwise indicated. Combinations of substituents that are constituents of the compounds of the present invention are permissible only if such combinations result in a stable compound.

The parenthetical nomenclature used in the definition of substituents such as $R^1$ (e.g., (H,OH)) is intended to reflect the substituents on both valences of the relevant atom. The invention is not limited to particular isomers and the order of moieties in the parentheses does not suggest a particular configuration.

The preferred compound of the present invention, known as 7-demethoxy-7,8-dehydro rapamycin, is a compound of Formula II wherein:

$R^1$, $R^2$ is (OH,H)
$R^3$, $R^4$ is =O
$R^5$, $R^6$ is =O

The compounds of this invention can exist in free form or, where appropriate, in salt form. Pharmaceutically acceptable salts and their preparation are well-known to those of skill in the art. The pharmaceutically acceptable salts of the compounds of this invention include the conventional non-toxic salts or the quaternary ammonium salts of such compounds which are formed, for example, from inorganic or organic acids of bases.

cording to well-known principles governing the protection of functional groups during synthesis. In Schemes A–D, the elaboration of such substituents is illustrated prior to the formation of the tetraenyl ring structure. The reagents utilized are either described in the literature or are commercially available.

Rapamycin derivatives reduced at the C-30 position may be prepared by treatment of rapamycin with a mixture of cerium trichloride and sodium cyanoborohydride. Suitable solvents for this reaction include a mixture of acetic acid and tetrahydrofuran. This reaction is illustrated in Scheme A with rapamycin shown as the starting material; however other rapamycin derivatives may be reduced at the C-30 position using this method.

Scheme A

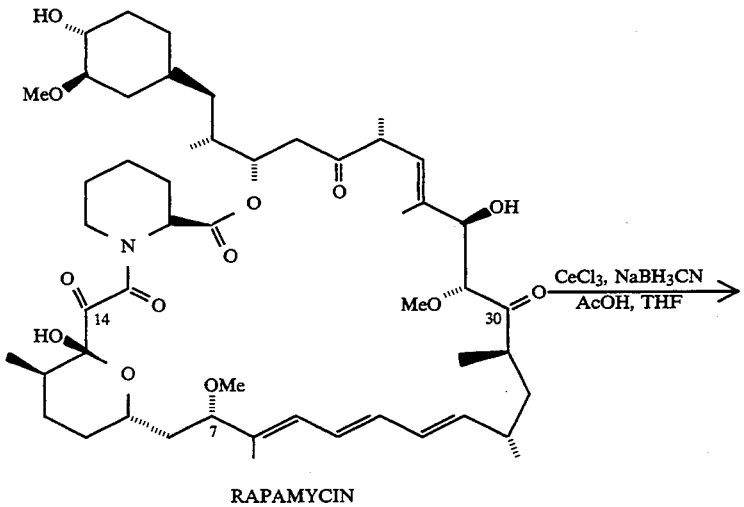

RAPAMYCIN

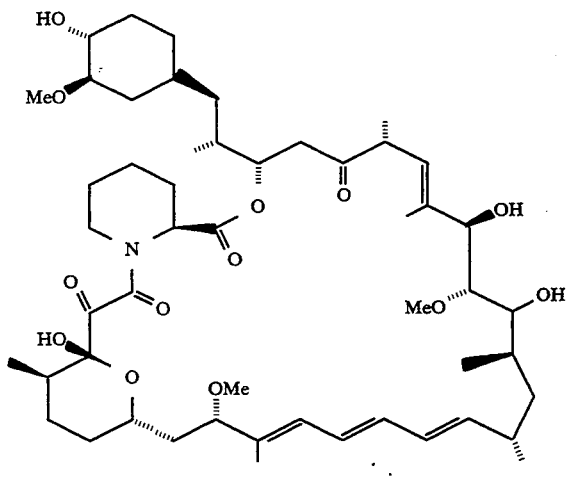

The compounds of the invention may form hydrates or solvates. It is known to those of skill in the art that charged compounds form hydrated species when lyophilized with water, or form solvated species when concentrated in a solution with an appropriate organic solvent.

The compounds of this invention may be prepared from rapamycin or a suitably substituted derivative thereof by the methods outlined below or conventional variations thereof. In general, the tetraenyl ring structure of the present compounds may be introduced either before or after elaboration of the ring substituents ac- Compounds of the invention which are reduced at both the C-14 and C-30 positions (i.e., $R^3$, $R^4$ and $R^5$, $R^6$=(H,OH)) may be prepared by the action of diisobutylaluminum hydride on rapamycin or a derivative thereof. By appropriate control of the same reduction method (limiting reaction times and amounts of reducing agent) compounds reduced only at the C-14 position can be prepared. This reaction is illustrated (reduction at both C-14 and C-30 positions shown), with rapamycin shown as the starting material, in Scheme B.

Scheme B

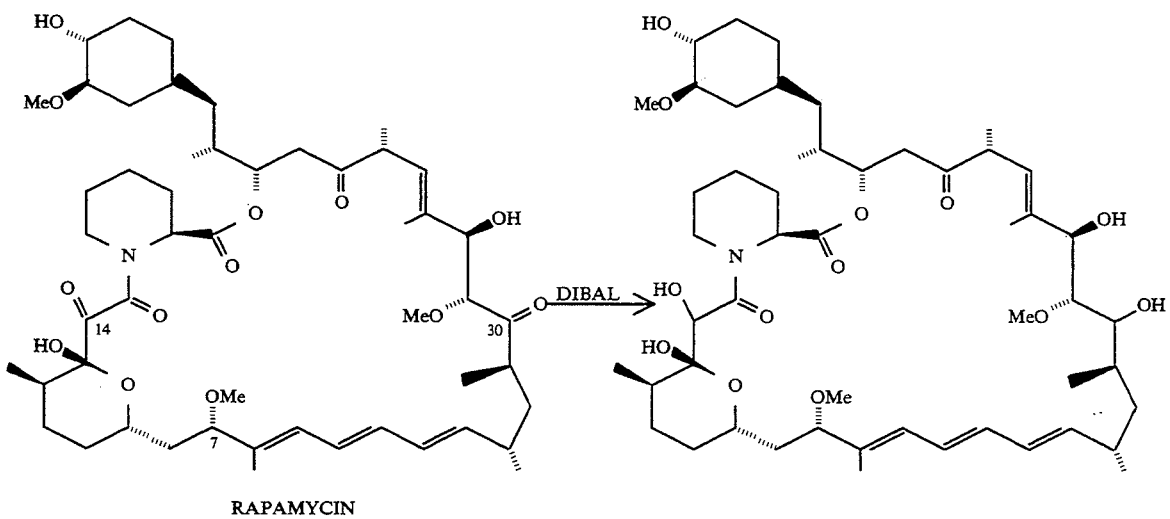

Certain compounds of the invention may be prepared from novel phenylthionocarbonate intermediates. The preparation of these intermediates, and their conversion to compounds of the invention is illustrated in Scheme C. As shown in Scheme C, rapamycin (although a derivatized rapamycin could also be utilized) is contacted with phenylchlorothionoformate in the presence of a base such as dimethylaminopyridine (DMAP) to prepare rapamycin derivatized at C-28 and/or C-43 atoms. These intermediates may be converted to compounds of this invention by reaction with a free-radical-based reductant such as trialkyltin hydride or tris(trimethylsilyl)silane and a radical initiator such as azobisisobutyronitrile (AIBN), benzoyl peroxide or triethylborane.

Scheme C

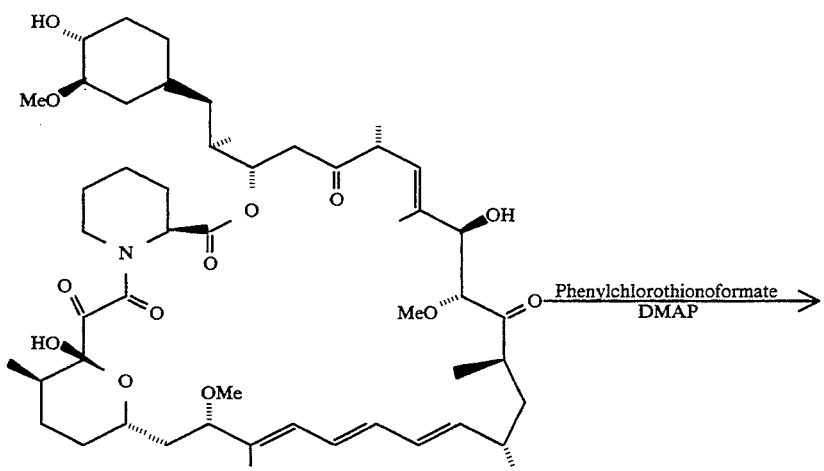

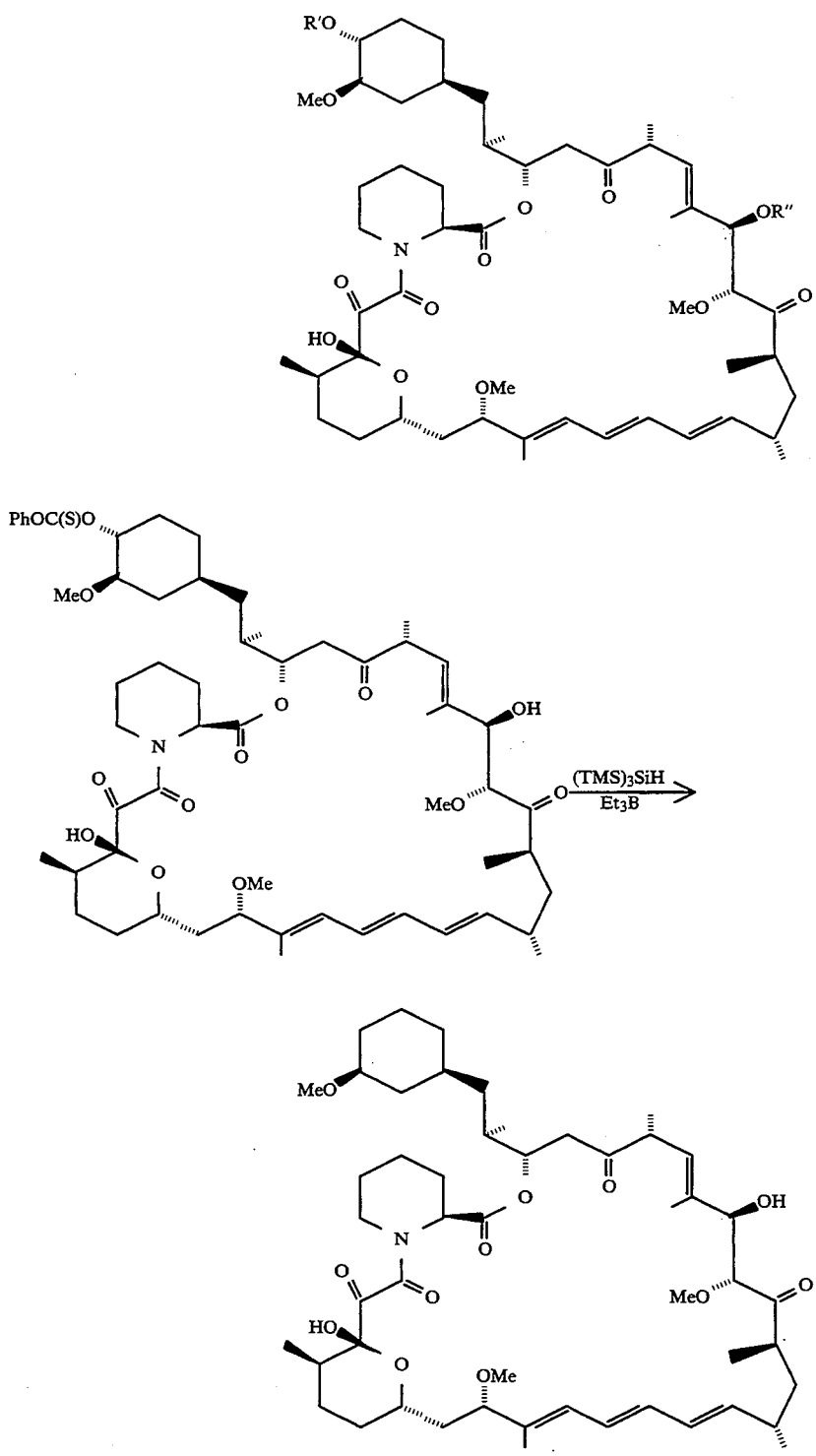
Compounds of the invention with an oxy (=O) moiety at C-43 may be prepared as illustrated in Scheme D. Scheme D illustrates the preparation of 43-dehydrorapamycin, which is useful as an intermediate for preparing other compounds of the invention.

Scheme D

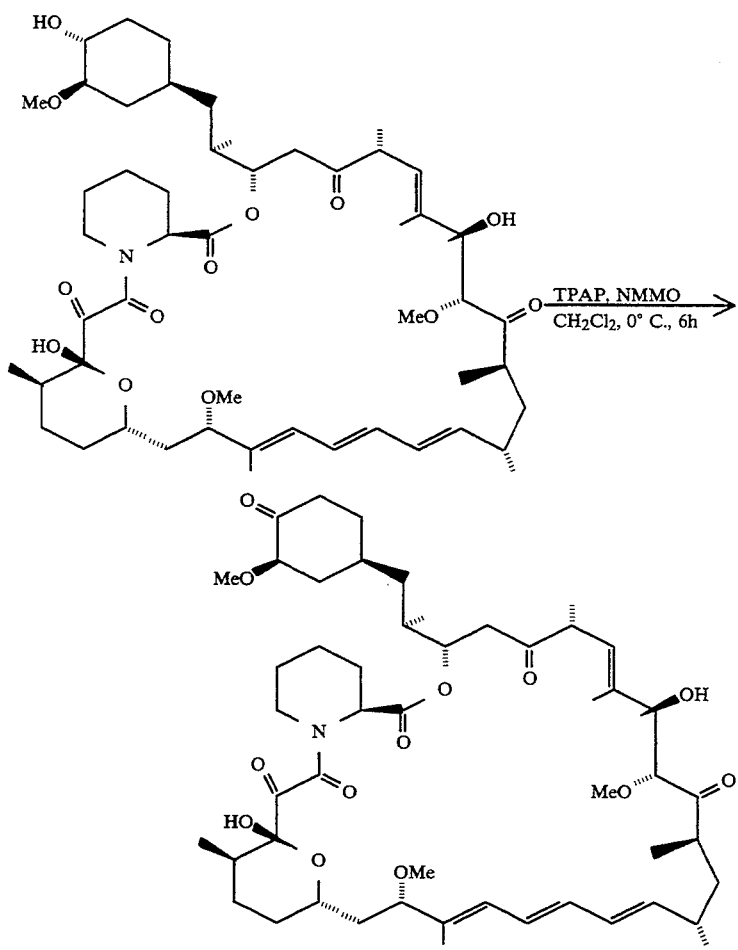

High concentration of lithium perchlorate in diethyl ether has been reported to be an efficient method to promote a number of synthetic transformations under mild conditions; recent literature examples include Diels-Alder cycloadditions, ionization reactions and [1,3] sigmatropic rearrangements (P. A. Grieco et al., *J. Am. Chem. Soc.* 1990, 112, 4595 and 1991, 113, 5488.).

The tetraenyl ring structure of the compounds of the present invention can be prepared by subjection of rapamycin to the action of highly concentrated (3–5M) solution of lithium perchlorate in anhydrous diethyl ether. The reaction works more efficiently in the presence of a small amount of acetic acid. Under these conditions elimination of the elements of methanol takes place, resulting in the generation of C7–C8 double bond.

The Examples provided below in this specification provide a variety of synthetic methods for preparing compounds of this invention.

This invention also relates to pharmaceutical compositions comprising a pharmaceutically acceptable carrier or excipient and an effective amount of one or more compounds of Formula II.

A compound of Formula II is administered in conventional dosage form prepared by combining a therapeutically effective amount of the compound ("active ingredient") with standard pharmaceutical carriers or excipients according to conventional procedures. These procedures may involve mixing, granulating and compressing or dissolving the ingredients as appropriate to the desired preparation.

The pharmaceutical carrier employed may be, for example, either a solid or liquid. Exemplary of solid carrier are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or excipient may include time delay material well known to the art, such as glyceryl monostearate or glyceryl distearate along or with a wax, ethylcellulose, hydroxypropylmethylcellulose, methylmethacrylate and the like.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of a compound of the present invention is dissolved in an aqueous solution of an organic or inorganic acid, such as a 0.3M solution of succinic acid, or, preferably, citric acid. Alternatively, acidic derivatives can be dissolved in suitable basic solutions. If a soluble salt form is not available, the compound of the present invention is dissolved in a suitable cosolvent or combinations thereof. Examples of such suitable cosolvents include, but are not limited to, alcohol, propylene glycol, polyethylene glycol 300, polysorbate 80, glycerin and the like in concentrations ranging from 0–60% of the total volume.

Tests indicate that the compounds of this invention are useful in prophylactically or therapeutically inhibiting the growth of pathogenic fungi in a human or other animal in need thereof. The invention, therefore, includes methods of inhibiting the growth of pathogenic fungi in a human or other animal in need thereof which comprises administering to such human or animal an effective, non-toxic amount of a compound of Formula II.

By the term "pathogenic fungi" is meant fungi capable of producing disease in a human or other animal. Examples of pathogenic fungi include, but are not limited to *Candida albicans* and other candida species, *Microsporum gypseum*, *Trichophyton mentagrophytes*, Asperqillus sp. and Sporotrichum sp. The ability of the compounds of this invention to inhibit the growth of pathogenic fungi may be demonstrated or predicted by standard tests known and used for this purpose, for example, the yeast assay described hereinbelow.

One skilled in the art would be able, by routine experimentation, to determine what an effective, non-toxic amount of compound would be for the purpose of inhibiting pathogenic fungi growth. Generally, however, an effective dosage will be in the range of about 0.05 to 100 milligrams per kilogram body weight per day.

Tests indicate that the compounds of this invention are also useful for inducing immunosuppression, i.e., inducing a suppression of a human's or animal's immune system. This invention therefore relates to a method of prophylactically or therapeutically inducing immunosuppression in a human or other animal in need thereof which comprises administering an effective, non-toxic amount of such a compound of this invention to such human or other animal.

The ability of the compounds of this invention to induce immunosuppression may be demonstrated in standard tests used for this purpose, for example, a mixed lymphocyte reaction test or a test measuring inhibition of T-cell proliferation measured by thimidine uptake.

The fact that the compounds of this invention have utility in inducing immunosuppression means that they are useful in the treatment or prevention of resistance to or rejection of transplanted organs or tissues (e.g., kidney, heart, lung, bone marrow, skin, cornea, etc.); the treatment or prevention of autoimmune, inflammatory, proliferative and hyperproliferative diseases, and of cutaneous manifestations of immunologically mediated diseases (e.g., rheumatoid arthritis, lupus erythematosus, systemic lupus erythematosus, Hashimotos thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, Lichen planus, Pemplugus, bullous Pemphigold, Epidermolysis bullosa, uritcaris, angiodemas, vasculitides, erythemas, cutaneous eosinophilias, Alopecia areata, etc.); the treatment of reversible obstructive airways disease, intestinal inflammations and allergies (e.g., Coeliac disease, proctitis, eosinophilia gastroenteritis, mastocytosis, Chrohn's disease and ulcerative colitis) and food related allergies (e.g., migrane, rhinitis, and eczema).

One skilled in the art would be able, by routine experimentation, to determine what an effective, non-toxic amount of compound would be for the purpose of inducing immunosuppression. Generally, however, an effective dosage will be in the range of about 0.05 to 100 milligrams per kilogram body weight per day.

The compounds of the invention may be administered to a human or other animal in accordance with the aforementioned methods of treatment in an amount sufficient to produce such effect to a therapeutic or prophylactic degree. Such compound of the invention can be administered to such human or other animal in a conventional dosage form prepared by combining the compound of the invention with a conventional pharmaceutically acceptable carrier or excipient according to known techniques. It will be recognized by one of skill in the art that the form and character of the pharmaceutically acceptable carrier or excipient is dictated by the amount of active ingredient with which it is to be combined, the route of administration and other well-known variables.

The route of administration of the compound of the invention may be oral, parenteral, by inhalation or topical. The term parenteral as used herein includes intravenous, intramuscular, subcutaneous, rectal, vaginal or intraperitoneal administration. The subcutaneous and intramuscular forms of parenteral administration are generally preferred.

The daily parenteral and oral dosage regimens for employing compounds of the present invention to prophylactically or therapeutically inhibit the growth of pathogenic fungi, or to prophylatically or therapeutically induce immunosuppression will generally be in the range of about 0.05 to 100, but preferably about 0.5 to 10, milligrams per kilogram body weight per day.

The compounds of the present invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 10 to 100 milligrams.

The compounds of the present invention may also be administered topically. By topical administration is meant non-systemic administration and includes the application of a compound of the present invention externally to the epidermis, to the buccal cavity and instillation of such a compound into the ear, eye and nose, and where the compound does not significantly enter the blood stream. By systemic administration is meant oral, intravenous, intraperitoneal and intramuscular administration. The amount of a compound of the invention (hereinafter referred to as the active ingredient) required for therapeutic or prophylactic effect on pathogenic fungi growth inhibition or immunosuppression induction upon topical administration will, of course, vary with the compound chosen, the nature and severity of the condition being treated and the animal undergoing treatment, and is ultimately at the discretion of the physician. A suitable topical dose of a compound of the invention will generally be within the range of about 1 to 100 milligrams per kilogram body weight daily.

While it is possible for an active ingredient to be administered alone as the raw chemical, it is preferable to present it as a pharmaceutical formulation. The active ingredient may comprise, for topical administration, from 0.001% to 10% w/w, e.g., from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefore and optionally any other therapeutic ingredient(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90–100 C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surface active such as sorbitan esters or polyoxyethylene derivatives thereof. Suspending agents such as natural gums, cellulose derivatives or in organic materials such as silicaceous silicas, and other ingredients such as lanolin, may also be included.

It will be recognized by one of skill in the art that the optimal quantity and spacing of individual dosages of the compound of the invention will be determined by the nature and extent of the condition being treated, the form, route and site of administration, and the particular animal being treated, and that such optimums can be determined by conventional techniques. It will also be appreciated by one of skill in the an that the optimal course of treatment, i.e., the number of doses of the compound of the invention given per day for a defined number of days, can be ascertained by those skilled in the an using conventional course of treatment determination tests.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES

I. COMPOSITION EXAMPLES

Example A—Capsule Composition

A pharmaceutical composition of this invention in the form of a capsule is prepared by filling a standard two-piece hard gelatin capsule with 50 mg of a compound of the present invention, in powdered form, 100 mg of lactose, 32 mg of talc and 8 mg of magnesium stearate.

Example B—Injectable Parenteral Composition

A pharmaceutical composition of this invention in a form suitable for administration by injection is prepared by stirring 1.5% by weight of a compound of the present invention in 10% by volume propylene glycol and water. The solution is sterilized by filtration.

Example C—Ointment Composition

Compound of the invention 1.0 g
White soft paraffin to 100.0 g

The compound of the present invention is dispersed in a small volume of the vehicle and gradually incorporated into the bulk of the vehicle to produce a smooth, homogeneous product. Collapsible metal tubes are then filled with the dispersion.

Example D—Topical Cream Composition

Compound of the present invention 1.0 g
Polawax GP 200 20.0 g
Lanolin Anhydrous 2.0 g
White Beeswax 2.5 g
Methyl hydroxybenzoate 0.1 g
Distilled Water to 100.0 g The polawax, beeswax and lanolin are heated together at 60 C. A solution of methyl hydroxybenzoate is added and homogenization is achieved using high speed stirring. The temperature is then allowed to fall to 50 C. The compound of the present invention is then added and dispersed throughout, and the composition is allowed to cool with slow speed stirring.

Example E—Topical Lotion Composition

Compound of the present invention 1.0 g
Sorbitan Monolaurate 0.6 g
Polysorbate 20 0.6 g
Cetostearyl Alcohol 1.2 g Glycerin 6.0 g
Methyl Hydroxybenzoate 0.2 g
Purified Water B.P. to 100.00 ml The methyl hydroxybenzoate and glycerin are dissolved in 70 ml of the water at 75. The sorbitan monolaurate, polysorbate 20 and cetostearyl alcohol are melted together at 75 C and added to the aqueous solution. The resulting emulsion is homogenized, allowed to cool with continuous stirring and the compound of the present invention is added as a suspension in the remaining water. The whole suspension is stirred until homogenized.

Example F—Eye Drop Composition

Compound of the present invention 0.5 g
Methyl Hydroxybenzoate 0.01 g
Propyl Hydroxybenzoate 0.04 g
Purified water B.P. to 100.00 ml (B.P.=British Pharmacopia)

The methyl and propyl hydroxybenzoates are dissolved in 70 ml purified water at 75 C and the resulting solution is allowed to cool. The compound of the present invention is then added, and the solution is sterilized by filtration through a membrane filter (0.22 mu m pore size) and packed aseptically into suitable sterile containers.

Example G—Composition for Administration by Inhalation

For an aerosol container with a capacity of 15–20 ml: Mix 10 mg of a compound of the present invention with 0.2–0.2% of a lubricating agent, such as polysorbate 85 or oleic acid, and disperse such mixture in a propellant, such as freon, preferably in a combination of (1,2 dichlorotetrafluoroethane) and difluorochloromethane and put into an appropriate aerosol container adapted for either intranasal or oral inhalation administration.

Example H—Composition for Administration by Inhalation

For an aerosol container with a capacity of 15–20 ml: Dissolve 10 mg of a compound of the present invention in ethanol (6–8 ml), add 0.1–0.2% of a lubricating agent, such as polysorbate 85 or oleic acid; and disperse such in a propellant, such as freon, preferably a combination of (1.2 dichlorotetrafluoroethane) and difluorochloromethane, and put into an appropriate aerosol container adapted for either intranasal or oral inhalation administration.

II. SYNTHETIC EXAMPLES

In the following Examples, rapamycin was obtained via fermentation, and all other starting materials and chemical reagents were obtained from commercial suppliers unless otherwise indicated.

Example 1

Preparation of 7-Demethoxy-7,8-dehydrorapamycin

To a suspension of rapamycin (4.0 g, 4.37 mmol) in anhydrous ether (79 mL was added anhydrous lithium perchlorate (42.2 g, 396.6 mmol) and a small amount of acetic acid (67 mg, 1.1 mmol) and the resulting solution was stirred at room temperature for 3 h. The reaction mixture was diluted with water and extracted with methylene chloride. The organic layer was washed with brine, dried over anhydrous $MgSO_4$ and concentrated to a yellow solid. The crude material was purified by reversed-phase chromatography (Rainin Dynamax-60A 8 μm C18); elution with 87:13 MeOH:water provided the title compound as a white powder (1.27 g, 33%). $^1$HNMR ($CDCl_3$, 400 MHz, 2.5:1 mixture of trans:cis amide rotamers; data for the trans-rotamer): δ6.48 (dd, J=14.4, 11.5 Hz, 1H), 6.26 (dd, J=14.4, 10.9 Hz, 1H), 6.23 (d, J=15.8 Hz, 1H), 6.19 (d, J=11.5 Hz, 1H), 6.12 (dd, J=15.0, 10.9 Hz, 1H), 5.77 (dd, J−15.8, 3.6 Hz, 1H), 5.43 (dd, J−15.0, 9.0 Hz, 1H), 5.41 (d, J=10.0 Hz, 1H), 5.20 (d, J=5.1 Hz, 1H), 5.14 (m, 1H), 4.58 (br d, J=10.1 Hz, 1H), 4.24 (d, J=4.1 Hz, 1H), 3.99 (d, J=4.1 Hz, 1H), 3.45 (br d, J=14.5 Hz, 1H), 3.40 (s, 3H), 3.33 (s, 3H), 3.16 (dq, J=10.0, 6.6 Hz, 1H), 2.64 (dd, J=17.5, 4.5 Hz, 1H), 2.35 (dd, J=17.5, 7.0 Hz, 1H), 1.83 (s, 3H), 1.72(s, 3H), 1.07 (d, J=6.6 Hz, 3H), 1.02 (d, J=6.6 Hz, 3H), 0.96 (d, J=6.6 Hz, 3H), 0.92 (d, J=6.6 Hz 3H), 0.86 (d, J=6.6 Hz, 3H), 0.62 (q, J=12.0 Hz, 1H); $^{13}$CNMR ($CDC_{13}$, 100.6 MHz, 3:1 mixture of trans:cis amide rotamers; data for the trans-rotamer): δ212.4, 207.5, 196.8, 169.7, 165.9, 139.2, 135.2, 134.7, 133.3, 130.9, 130.7, 129.5, 127.9, 126.0, 99.0, 84.4, 83.9, 76.4, 74.8, 73.9, 69.3, 58.2, 56.7, 51.9, 45.9, 44.4, 41.9, 21.3, 21.0, 16.1, 15.9, 15.8, 15.6, 14.3, 13.7, 12.9; MS (ESI+/$NH_4OAc$) m/z 904 ($M+NA^+$), 899 ($M+NH_4^+$), 882, 864; MS (ESI−/$NH_4COOH$) m/z 926 ($M+HCOO^{31}$); UV (MeOH) $\lambda$max 294, 309, 324 nm.

III. BIOLOGICAL EXAMPLES

The preferred compound of the present invention was analyzed for antifungal and immunosuppressive activity using the following assays.

Assay for Antifungal Activity

Yeast organism (*Saccharomyces cerevisiae*) in logarithmic growth were plated on complete agar medium (YPD). The compound was dissolved in an appropriate aqueous or organic solvent were placed in wells punched in the agar. Plates were incubated for 48 hours and zones of inhibition were measured.

Mitogenesis Assay for Immunosuppressive Activity

Spleen cells from BDF1 female mice were established in RPMI with 10% fetal calf serum at $5\times10^6$/mL. One hundred μL aliquots of this suspension ($5\times10^5$ cells) were dispensed into 96-well round-bottomed microliter plates (Linbro, Flow Laboratories). Concanavalin A (5 μg/ml)was added as the mitogenic stimulus, and the final volume in the microtiter wells was adjusted to 200 μL with RPMI. Cell cultures were incubated for 72 hours at 37° C. in a 5% $CO_2$ atmosphere and pulsed with 0.5μCi $^3$H-thymidine (specific activity 2.00 Ci/mole) for the last 18 hours of the 72 hour culture. The cells were harvested on an automated multiple sample harvester and cell-associated radioactivity counted in a Beckman liquid scintillation counter. The results are expressed as the mean values derived from quadruplicate measurements. Cell viability was determined by trypan blue exclusion after 72 hours of incubation. The compound to be tested was added to the microtiter plates at the appropriate dilutions prior to the addition of cells.

BIOLOGICAL DATA

The preferred compound showed in $IC_{12}$ of 7 ng/mL against *Saccharomyces cerevisae* and $IC_{50}$ of 7 nM in the mitogenesis assay. $IC_{12}$ refers to the concentration of drug in the aforementioned antifungal agar diffusion assay which produces a 12 mm zone of inhibition. These results indicate that the compound has both antifungal and immunomodulatory activity.

The above description and Examples fully disclose the present invention and preferred embodiments thereof, including how to make and use the present invention. However, it is understood that the present invention is not limited to the particular embodiments described herein above, but includes all modifications thereof within the scope of the following claims.

What is claimed is:

1. A compound of the formula wherein:
$R^1$ and $R^2$ are selected from the group consisting of =O, (—OH,H) and (H,H);
$R^3$ and $R^4$ are selected from the group consisting of =O, (H,H) and (H,OH);and
$R^5$ and $R^6$ are selected from the group consisting of =O and (H,OH); and all pharmaceutically acceptable salts, hydrates or solvates thereof.

2. A compound of claim 1 where $R^1$, $R^2$ are (OH,H).

3. A compound of claim 1 where $R^3$ together with $R^4$ is =O.

4. A compound of claim 1 where $R^5$ taken together with $R^6$ is =O.

5. A compound of claim 1 wherein:
$R^1$, $R^2$ is (OH,H)
$R^3$, $R^4$ is =O
$R^5$, $R^6$ is =O 6. A pharmaceutical composition comprising a pharmaceutically acceptable carrier or excipient, and an effective therapeutic or prophylatic amount of one or more compounds of claim 1.

7. A pharmaceutical composition comprising a pharmaceutically acceptable carrier or excipient and an effective therapeutic or prophylactic amount of a compound of claim 2.

8. A pharmaceutical composition comprising a pharmaceutically acceptable carrier or excipient and an effective therapeutic or prophylactic amount of a compound of claim 3.

9. A pharmaceutical composition comprising a pharmaceutically acceptable carrier or excipient and an effective therapeutic or prophylactic amount of said compound of claim 4.

10. A pharmaceutical composition comprising a pharmaceutically acceptable carrier or excipient and an effective therapeutic or prophylactic amount of said compound of claim 5.

11. A method of inhibiting the growth of pathogenic fungi in a human or other animal in need thereof which comprises administering to such human or other animal an effective, non-toxic amount of a compound of claim 1.

12. A method of inhibiting the growth of pathogenic fungi in a human or other animal in need thereof which comprises administering to such human or other animal an effective, non-toxic amount of a compound of claim 5.

13. A method of inducing immunosuppression in a human or other animal in need thereof which comprises administering to such human or other animal an effective, non-toxic amount of a compound of claim 1.

14. A method of inducing immunosuppression in a human or other animal in need thereof which comprises administering to such human or other animal an effective, non-toxic amount of a compound of claim 5.

15. A method of preparing a compound of claim 1 comprising contacting rapamycin or a suitably substituted derivative thereof with a highly concentrated solution of lithium perchlorate.

16. A method of claim 15 wherein said concentration of said lithium perchlorate is about 3–5M.

17. A method of claim 16 wherein said lithium perchlorate is dissolved in anhydrous diethyl ether to form a solution.

18. A method of claim 17 further comprising addition of a small amount of acetic acid to said solution.

* * * * *